(12) United States Patent
Müller

(10) Patent No.: US 6,664,106 B1
(45) Date of Patent: Dec. 16, 2003

(54) PRODUCTION OF PRIMMORPHS FROM DISASSOCIATED CELLS OF SPONGES AND CORALS

(76) Inventor: Werner E. G. Müller, Semmelweisstrasse 12, 65203 Wiesbaden (DE)

( * ) Notice: Subject to any disclaimer, the term of this patent is extended or adjusted under 35 U.S.C. 154(b) by 0 days.

(21) Appl. No.: 09/701,974

(22) PCT Filed: May 6, 1999

(86) PCT No.: PCT/EP99/03121

§ 371 (c)(1),
(2), (4) Date: Nov. 30, 2000

(87) PCT Pub. No.: WO99/63060

PCT Pub. Date: Dec. 9, 1999

(30) Foreign Application Priority Data

May 30, 1998 (DE) ......................... 198 24 384

(51) Int. Cl.⁷ ................................. C12N 5/06
(52) U.S. Cl. .................. 435/325; 435/378; 435/379; 435/383
(58) Field of Search ................. 435/325, 378, 435/379, 383

(56) References Cited

FOREIGN PATENT DOCUMENTS

DE          3230527 A    *   2/1994

OTHER PUBLICATIONS

Sipkema et al., 'Primmorphs from seven marine sponges: formation and structure,' Journal of Biotechnology, 100:127–139 (2003).
Osinga et al., Cultivation of marine sponges for metabolite production: application for biotechnology? (Mar. 1998) TIBTECH, vol. 16, 130–134.*
Osinga et al., Cultivation of marine sponges (1999) Marine Biotechnology, vol. 1, pp. 509–532.*
Muller et al, Establishment of primary cell culture from a sponge: primmorphs from suberites domuncula (Mar. 17, 1999) Mar Ecol Prog Ser, vol. 178, pp. 205–219.*
Muller er al., Chemosensitizers of the multixenobiotic resistance in the amorphous aggregates (marine snow): etiology of mass killing on the benthos in the northern atlantic (Dec. 1998) Env Tox and Parma, vol. 6, pp. 229–238.*
Fujita et al., Aggregation of dissociated sea urchins and sponge cells by culture fluids of microorganisms having hemaglutination activity (1972) J. Gen. Appl. Microbiol., vol. 18, pp. 77–79.*
Thomassen et al., Growth and energetics of the sponge halichondria panicea (1995) Mar Ecol Prog Ser, vol. 128, pp. 239–246.*
Muller et al, Species specific aggregation factor in sponges V. influence on programmes syntheses (Jan 1976) BBA, vol. 418, pp. 217–225.*

Imseicke et al., Formation of spicules by sclerocytes from the freshwater sponge ephydatia muelleri in short term cultures in vitro (Jul./Aug. 1995) In Vitro Cell. Dev. Biol.–Animal, vol. 31, pp. 528–535.*
Wilson, On some phenomena of coalescence and regeneration in sponges (1907) J. Exp. Zool., vol. V, No. 2, pp. 245–258.*
Pompani et al. (1994) Sponge cell culture for production bioactive metabolites, In Sponges in Time and Space, Van Soest, RWM, Van Kempen, TMG, and Braekman (eds) Rottertdam: AA Balkema, 395–400.*
Oland et al. (1994) Growth and interactions of cells from insect nervous system in vitro, In Insect Cell Biotechnology, Maramorosch and McIntosh (eds) Boca Raton: CRC press, 105–125.*
Rinkevich, 'Cell cultures from marine invertebrates: obstacles, new approaches and recent improvements,' Journal of Biotechnology, 70:133–153 (1999).
Custodio et al., 'Evolution of Cell Adhesion Systems: Evidence for Arg–Gly–Asp–Mediated Adhesion in the Protozoan *Neoparamoeba aestuarina* , ' J. Euk. Microbiol., 42(6):721–4 (1995).
Klautau et al., 'In vitro culture of primary cell lines from marine sponges,' Sponges in Time and Space, van Soest, van Kempen & Braekaman (eds.), Balkema, Rotterdam (1994).
Custodio et al., "Primmorphs generated from dissociated cells of the sponge *Suberites domuncula*: a model system for studies of cell proliferation and cell death," Mechanisms of Ageing and Development, 105:45–59 (1998).

(List continued on next page.)

Primary Examiner—Irene Marx
(74) Attorney, Agent, or Firm—Kriegsman & Kriegsman

(57) ABSTRACT

This invention relates to the establishment of a novel method of culturing sponge cells, coral cells and cells from other invertebrates in vitro. The cells cultured in vitro, which can be cultured as units similar to aggregates, are referred to as primmorphs. The method makes the following methods possible for the first time, using cells/aggregates/primmorphs from sponges, corals and other invertebrates:

Methods (i) of preparing substances which modulate proliferation and DNA synthesis,
(ii) of identifying/detecting environmentally harmful substances,
(iii) of culturing bacteria and other micro-organisms,
(iv) of preparing asexual reproductive bodies that can be used in aquaculture for growing corresponding organisms,
(v) of preparing cell libraries,
(vi) of optimising the nutritional requirements of the cells/aggregates/primmorphs, and
(vii) of identifying substances which modulate telomerase activity in cells/aggregates/primmorphs.

1 Claim, No Drawings

OTHER PUBLICATIONS

Wimmer et al., "Origin of the integrin–mediated signal transduction," Eur. J. Biochem., 260:156–165 (1999).

Müller et al., "Cell Membranes in Sponges," International Review of Cytology, 129–181 (1982).

Müller et al., "Species–Specific Aggregation Factor in Sponges," Differentiation, 10:55–60 (1978).

Koziol et al., "Sponges (Porifera) model systems to study the shift from immortal to senescent somatic cells: the telomerase activity in somatic cells," Mechanisms of Ageing and Development, 100:107–120 (1998).

Müller et al., "Aggregation of Sponge Cells," Experimental Cell Research, 113:409–414 (1978).

Gamulin et al., "Cell Adhesion Receptors and Nuclear Receptors Are Highly Conserved from the Lowest Metazoa (Marine Sponges) to Vertebrates," Biol. Chem. Hoppe–Seyler, 375:583–588 (1994).

Ilan et al., "Progress towards cell cultures from a marine sponge that produces bioactive compounds," J. Mar. Biotechnol., 4:145–149 (1996).

* cited by examiner

PRODUCTION OF PRIMMORPHS FROM DISASSOCIATED CELLS OF SPONGES AND CORALS

DESCRIPTION

1. Introduction

This invention relates to the establishment of the first and therefore novel method of culturing sponge cells, coral cells and cells from other invertebrates in vitro. The cells cultured in vitro, which can be cultured as units similar to aggregates, are referred to as primmorphs. A method is thus available which makes it possible for the first time, using cells/aggregates/primmorphs from sponges, corals and other invertebrates, to introduce methods: (i) of preparing substances which modulate proliferation and DNA synthesis, (ii) of identifying/detecting environmentally harmful substances, (iii) of culturing bacteria and other microorganisms, (iv) of preparing asexual reproductive bodies that can be used in aquaculture for growing corresponding organisms, (v) of preparing cell libraries, (vi) of optimising the nutritional requirements of the cells/aggregates/primmorphs, and (vii) of identifying substances which modulate telomerase activity in cells/aggregates/primmorphs.

The phylum Porifera (sponges), together with the other metazoan phyla has a monophyletic origin, [Müller W. E. G. (1995) Naturwissenschaften 82, 321–329]. A fundamental autapomorphic feature of the metazoa, including the Porifera, is, for example, the presence of the receptor tyrosine kinase, which can only be found in metazoa [Müller W. E. G., Schäcke H. (1996) Prog. Molec. Subcell. Biol. 17, 183–208].

Within the metazoa, the Porifera exhibit a plesiomorphic feature which can be found in no other higher phylum of metazoa; all (or almost all) their cells have a high level of telomerase activity [Koziol C., Borojevic R., Steffen R., Müller W. E. G. (1998) Mech. Ageing Develop. 100, 107–120]. In principle, this is an indication that sponge cells cannot be subdivided into gametes or somatic cells [Müller W. E. G. (1998a) Progr. Molec. Subcell. Biol. 19, 98–132; Müller W. E. G. (1998b) Naturwiss. 85:11–25]. In higher metazoa not suffering from tumours, virtually only the gametes are always telomerase-positive, whereas the somatic cells are telomerase-negative [Lange T. v. (1998) Science 279,334–335].

Because of this property that all (or virtually all) sponge cells are telomerase-positive, it might be presumed that sponge cells are immortal. So far, however, there has not yet been any report of neoplastic diseases in sponges [De-Flora S., Bagnasco M., Bennicelli C., Camoirano A., Bojnemirski A., Kurelec B. (1995). Mutagenesis 10, 357–364]. In the very first report on the high telomerase activity in sponges, it was shown by our group that, when removed from their associated tissue and converted into a dissociated state, the cells become telomerase-negative [Koziol C., Borojevic R., Steffen R., Müller W. E. G. (1998) Mech. Ageing Develop. 100, 107–120]. Cells in a single-cell suspension very probably die off through apoptosis [Wagner C., Steffen R., Koziol C., Batel R., Lacorn M., Steinhart H., Simat T., Müller W. E. G. (1998) Marine Biol. 131, 411–421]. In addition, the fact that sponges have a species-specific blueprint led us to postulate that sponges are equipped with an apoptosis mechanism to replace a certain group of cells at a specific time. This assumption was supported by the finding that cells in the sponge tissue are induced to effect apoptosis in response to endogenous factors (e.g. the addition of heat-treated bacteria) and to exogenous factors (cadmium) [Wagner C., Steffen R., Koziol C., Batel R., Lacorn M., Steinhart H., Simat T., Müller W. E. G. (1998) Marine Biol. 131,411–421].

After it had been demonstrated by our group that sponge cells possess high telomerase activity [Koziol C., Borojevic R., Steffen R., Müller W. E. G. (1998) Mech. Ageing Develop. 100, 107–120], it appeared an easily achievable aim to establish a sponge cell culture. Up to now, however, it has only been possible to keep sponge cells alive, as in the case of the species *Hymeniacidon heliophila* [Pomponi S. A., Willoughby R. (1994) In: R. van Soest, A. A. Balkema (Eds.) Sponges in Time and Space, Rotterdam, Brookfield, pp.395–400], *Latrunculia magnifica* [Ilan M., Contini H., Carmeli S., Rinkevich B. (1996) J. Mar. Biotechnol. 4, 145–149] and *Suberites domuncula* [Müller W. E. G., Steffen R., Rinkevich B., Matranga V., Kurelec B. (1996) Marine Biol. 125, 165–170]. These cells do not, however, proliferate [Ilan M., Contini H., Carmeli S., Rinkevich B. (1996) J. Mar. Biotechnol. 4, 145–149].

One reason why, when kept in vitro, sponge cells have so far only remained in a quiescent state is, for example, that the methods of establishing the single-cell culture have been inappropriate, i.e. suitable culture conditions and culture media have not been available [Pomponi S. A., Willoughby R. (1994) In: R. van Soest, A. A. Balkema (Eds.) Sponges in Time and Space, Rotterdam, Brookfield, pp. 395–400; Ilan M., Contini H., Carmeli S., Rinkevich B. (1996) J. Mar. Biotechnol. 4, 145–149]. The media used were supplemented with foetal calf/bovine serum [Pomponi S. A., Willoughby R. (1994) In: R. van Soest, A. A. Balkema (Eds.) Sponges in Time and Space, Rotterdam, Brookfield, pp. 395–400; Ilan M., Contini H., Carmeli S., Rinkevich B. (1996) J. Mar. Biotechnol. 4, 145–149]. So far, it has been assumed that growth factors found in the serum of vertebrates also stimulate the cell growth of sponges and other invertebrates. This assumption does not, however, appear appropriate; the reason for this is our findings which show that sponge cells possess receptors on their surface that are activated by ligands which are different from those of mammalian receptors in general and human receptors in particular. Accordingly, it cannot be regarded as very probable that growth factors which occur in calf/bovine sera will have an effect on sponge receptors specifically and invertebrates in general. Furthermore, media rich in sera entail the risk of contamination with protozoa [Osinga R., Tramper J., Wijffels R. H. (1998) Trends Biotechnol. 16, 130–134].

What is surprising and novel is our finding, which is the subject matter of the present patent application, that in vitro conditions can be defined which lead to the formation of multicellular aggregates of sponges, corals and other invertebrates from dissociated single cells. The aggregates have an appearance similar to tissue and can be maintained in a culture for more than five months. These aggregates are referred to as primmorphs. In addition, we describe how cells, having associated themselves into primmorphs, become telomerase-positive and are capable of DNA synthesis/cell proliferation.

With the successful establishment of an in vitro culture of cells from sponges, corals and other invertebrates, a new route has been opened up for introducing methods of the kind specified at the beginning of this description.

2. Description of the Method

2.1. Material

Natural seawater (S9148), penicillin and streptomycin were obtained from Sigma (Deisenhofen; Germany), RNA-guard (24,000 units/ml) from Pharmacia (Freiburg; Germany), the "Telomerase Detection Kit" (TRAPeze) from Oncor (Gaithersburg, Md.; USA), "BrdU-labeling and detection kit" from Boehringer Mannheim (Mannheim; Germany) and SYBR Green I from Molecular Probes (Leiden; Netherlands).

The compositions of $Ca^{2+}$ and $Mg^{2+}$-free artificial seawater [CMFSW] and CMFSW to which ethylene diamine tetra-acetic acid (EDTA) was added [CMFSW-E] are as described earlier [Rottmann M., Schröder H. C., Gramzow M., Renneisen K., Kurelec B., Dorn A., Friese U., Müller W. E. G. (1987) EMBO J 6,3939–3944].

2.2. Keeping Sponges and Other Invertebrates

Samples of the marine sponge *Suberites domuncula* (Porifera, Demospongiae, Hadromerida) were collected in the Northern Adriatic near Rovinj (Croatia) and then kept in tanks in Mainz (Germany) at a temperature of 16° C.

As representatives of further invertebrates, the soft corals *Dendronephthya hemprichi* (Cnidaria, Anthozoa, Alcyonaria) were obtained from a pet shop and kept like sponges—with the exception of the temperature (22° C.).

As an example of sponges, corals and other invertebrates, the studies using the sponge *Suberites domuncula* and the soft coral *Dendronephthya hemprichi* are described here by way of example.

2.3. Dissociation of the Cells and Formation of the Primmorphs

All the materials and solutions/media are used under sterile conditions. Tissue samples [size usually 4 to 5 $cm^3$] from the sponge/soft coral are cut into smaller pieces [approx. 0.5–1 $mm^3$] of tissue with a scalpel in seawater. After this, these pieces are placed in conical 50 ml tubes [e.g. Falcon—catalogue number 2070] filled with CMFSW-E [ratio of tissue to medium usually 1:10. After gentle shaking, e.g. for 30 min. at 16° C. on a rotating shaker, the supernatant is decanted and discarded. The remaining pieces of tissue are once again mixed with new CMFSW-E in the same proportions and again gently shaken by rotation. The supernatant is decanted and discarded.

The pieces of tissue are now mixed with new CMFSW-E and again moved on a shaker, usually for 40 min. The supernatant, which contains the cells, is filtered through a nylon net with a mesh of e.g. 40 $\mu$m, and is trapped in a tube. This step of shaking the pieces of tissue in CMFSW-E and filtering the supernatant through a nylon net is repeated several times. The cell suspensions are mixed together and gently centrifuged in order to obtain the cells [usually at 500×g for 5 min.]. The cell suspension is placed in a seawater/antibiotic solution [antibiotic: usually 100 IU penicillin and 100 $\mu$g/ml streptomycin]. This step is usually repeated once or several times. The collected cells are harvested by centrifugation. A cell suspension is adjusted to $10^7$ cells/ml, and 1 ml thereof is usually placed in 5 ml seawater/antibiotic solution, e.g. in a 60 mm Petri dish [e.g. Falcon—catalogue number 3004].

The cells are incubated, usually at 16° C. and are usually transferred to a new Petri dish four times by careful resuspension with seawater/antibiotic solution. This is intended to ensure that the cells do not adhere to the dish. After aggregates have formed, these are transferred every day from the parent Petri dish which is now available, by pipetting into a conical tube [e.g. 15 ml tube (Falcon—catalogue number 2096)]. In the tube, the aggregates settle more quickly. After about 10 sec., the supernatant is decanted and the aggregate suspension is transferred to new Petri dishes. The aggregates are sucked up with a pipette and again washed once or several times, using the gravity method described, and resuspended in the seawater/antibiotic solution. It is possible to recover new aggregates from the parent Petri dish several times, usually two to five times. The rinsed aggregates remain in the Petri dishes until they have formed a smooth surface. Usually, the seawater/antibiotic solution is exchanged every day; two thirds of the solution are replaced by a fresh seawater/antibiotic solution.

Culturing under pressure has also proven suitable for promoting proliferation of the cells.

Following this, the aggregates now forming (primmorphs) (diameter about 1–3 mm) are transferred to 24-well plates [e.g. Nunclon™ (Nunc)—catalogue number 143982] and 1 ml seawater/antibiotic solution is added. One or two primmorphs are incubated per well.

If the cultures are stored under generally sterile conditions, it is possible to dispense with the addition of antibiotics to the seawater.

2.4. Incubation of the Primmorphs with BrdU

In order to determine the cell proliferation, the integration of BrdU [5-bromo-2'-deoxy-uridine] into the cellular DNA was measured using the "BrdU-iabeling and detection kit", in accordance with the manufacturer's instructions.

For this purpose, the primmorphs are incubated, usually in 1 ml of the seawater/antibiotic solution, which also contains the BrdU labelling solution [final dilution: usually 1:1,000 (10 $\mu$M of BrdU)]. The incubation period is usually 12 hours; the incubation itself is carried out in culture chambers [e.g. the "culture chamber slides (Nunc)"—catalogue number 177453]. Subsequently, the cells are dissociated in CFMSW-E, washed three times in CFMSW-E and fixed/denatured in 70% ethanol [pH 2.0]. After that, the cells are incubated with anti-BrdU mouse monoclonal antibodies and the immune complex is made visible with anti-mouse Ig coupled to alkaline phosphatase and with the dye substrate nitro-blue tetrazolium salt. The cells are analysed under a light-optical microscope.

2.5. Histological Examinations

The primmorphs are fixed in 4% paraformaldehyde/phosphate-buffered saline solution [Romeis, B. (1989) Mikroskopische Technik. Munich; Urban und Schwarzenberg]. After dehydration with ethanol, the primmorphs are embedded in Technovit 8100 [Beckstead J. H. (1985) J. Histochem. Cytochem. 9, 954–958]. Sections 2 $\mu$m thick are prepared and stained with Ziehl's fuchsin solution [Martoja R., Martoja M. (1967) Initiation aux Techniques de l'Histologie Animale. Prem. Ed. Masson et Cie., Paris].

2.6. Telomerase Approach

Telomerase activity is detected by means of polymerase chain reaction [PCR] using the "Telomerase Detection Kit (TRAPeze)"; details have already been described earlier (Kim N. W., Piatyszek M. A., Prowse K. R., Harley C. B., West M. D., Ho P. L. C., Coviello G. M., Wright W. E., Weinrich S. L., Shay J. W. (1994) Science 266:2011–2014; Koziol C., Borojevic R., Steffen R., Müller W. E. G. (1998) Mech. Ageing Develop. 100, 107–120]. The cell extracts added correspond to $5 \times 10^3$ cell equivalents. The amplification products are quantified by means of electrophoresis using a 12.5% non-denatured polyacrylamide gel in a 0.5× TBE buffer [performed in accordance with the manufacturer's instructions]. The gels are stained with SYBR Green I in order to detect DNA fragments [Molecular Probes (1996) MP 7567 Jul. 16, 1996]. The signals are quantified with a GS-525 Molecular Imager (Bio-Rad). The degree of telomerase activity is stated in TPG (total product generated) and is calculated as described [Oncor (1996) TRAPeze telomerase detection kit; catalogue no. S7700-Kit; second edition. Oncor, Gaithersburg, Md.; USA].

2.7. Statistics

The results were analysed for their significance by means of the paired Student's t-Test [Sachs L., Angewandte Statistik (Springer, Berlin) (1984)].

3. Detection of the Biochemical and Cytobiological Properties of the Primmorphs 3.1. Formation of Primmorphs From *S. domuncula* Cells Samples of the marine sponge *S. domuncula* were used to isolate the cells (FIG. 1A). Single cells were obtained by dissociation as described above. After the washing steps specified, the protozoa are removed, which tend to adhere to the surface of the plastic culture vessels. The cells are transferred to a seawater/antibiotic solution. After the total treatment/incubation period, usually five days, primmorphs form (FIG. 1D) from the cell aggregates (FIGS. 1B and C). The diameter of the cell aggregates after an incubation time of two days is about 100 $\mu$m (FIG. 1B) and continues to grow steadily in size; after four days, a diameter of 300 $\mu$m is usually reached (FIG. 1C). During this period, the aggregates round themselves off. Normally, after a further three to five days, primmorphs ranging between about 1 and 2 mm in size form (FIG. 1D).

Cross-sections through the primmorphs analysed under a microscope show that the cells in the interior are surrounded by a covering of epithelium-like cells several layers thick (FIGS. 1E and F). The cells which form from the squamous epithelium of the primmorphs are pinacocytes, as can be inferred from their flattened fusiform extremities with their distinct nuclei [survey: Simpson T. L. (1984) The Cell Biology of Sponges. Springer-Verlag, New York]; the size of the cells fluctuates around 20 to 30 $\mu$m. The cells within the primmorphs are mainly spherulous cells. They have a diameter of about 30 to 40 $\mu$m and are characterised by large round vacuoles which occupy the greater part of the cells. The other cells can be referred to as amoebocytes and archaeoeytes and are about 40 $\mu$m in size.

The outer appearance of the primmorphs is smooth and almost spherical (FIG. 1D); the histological sections show that the cells in the primmorphs are well organised into a tissue-like body (FIGS. 1E and F). It is striking that the squamous epithelium is formed by a layer several cells thick, usually consisting of pinacocytes (FIG. 1F), which is not found in natural sponges; this layer is delimited by a single-celled epithelium. The organised arrangement of the cells within the primmorphs also distinguishes them from the aggregates which are formed from dissociated cells in the presence of homologous aggregation factor [Müller W. E. G. (1982) Intern. Rev. Cytol. 77, 129–181].

In contrast to the asexual reproductive bodies, buds, reduction bodies and gemmulae formed in vivo [survey: Simpson T. L. (1984) The Cell Biology of Sponges. Springer-Verlag, New York], the primmorphs described here form in vitro from a suspension of individual cells. As is shown here, the dissociated cells form tissue-like bodies. The structure of functional primmorphs from a suspension of individual cells implies that this formation is an active process which comprises ejecting dead cells and cell fragments; this can be seen under a microscope as "ragged" edges round the primmorphs. The formation of a squamous epithelium from pinacocytes also indicates that sponge cells de-differentiate and subsequently re-differentiate, namely into those cells which are needed to form primmorphs.

The reorganisation of the cells during their reformation into primmorphs presupposes the presence of structures and associated proteins for cell migration; as an essential structural element for cell migration, collagen has been thoroughly documented in sponges. The existence of the adhesive glycoprotein fibronectin, which, in higher invertebrates and vertebrates, promotes cellular interactions with the extracellular matrix, including cell migration, has so far been shown for sponges by immunological cross-reactions with heterologous antibodies and by isolating the putative cDNA for that polypeptide from the sponge *Geodia cydonium* [Pahler S., Blumbach B., Müller I. M., Müller W. E. G. (1998) J. Exp. Zool.; in print]. The presence of inorphogens in primmorphs must be postulated in order to explain the precise arrangement of proliferating cells in these bodies. Recently, we isolated the cDNA which codes for a possible morphogen, namely "morphogen endothelial-monocyte-activating polypeptide", from the sponge *Geodia cydonium* (Pahler et al., 1998a).

3.2. Passaging of the Primmorphs

The primmorphs obtained from *S. domuncula* have so far been kept in culture for more than five months.

The primary primmorphs can be dissociated again into individual cells in CMFSW-E. The suspension of individual cells formed in this way is still capable of forming aggregates and subsequently primmorphs again, which are now called secondary primmorphs. This process occurs when the cells are transferred to a seawater/antibiotic solution. The kinetics of the formation of primmorphs are usually identical to those which were observed for primary primmorphs. Without $Ca^{2+}$, i.e. in CMFSW-E medium, the cells from primary primmorphs adhere weakly, after dissociation, to the surface of the culture vessels [e.g. Falcon catalogue number 3004]. For optimum adhesion, the vessels need to be gently roughened with a cover glass or a rubber scraper.

3.3. Level of Telomerase Activity in Cells as a Function of the Culture Conditions As described by us earlier [Koziol et al., 1998 (s. o.)], sponge cells go through a transition, after dissociation into individual cells, from a telomerase-positive state to a ielomerase-negative state.

The level of the telomerase activity was determined in the cells while primmorphs were forming from a single-cell suspension. The results show that cells in the natural cell association have a high level of telomerase activity; a quantitative analysis showed an activity of 8.9 TBG units/$5 \times 10^3$ cell equivalents (FIG. 2; lane a). When the telomerase activity was determined in cells which were left in a dissociated individual-cell state for 14 hours, the enzyme level dropped to 0.9 TBG units/$5 \times 10^3$ cell equivalents (FIG. 2; lane b). If, however, cells from primmorphs [about 10 days after their formation from single cells] were used for the analysis, the resulting telomerase activity was 4.7 TBG units/$5 \times 10^3$ cells (FIG. 2; lane c).

These results show that when released from their tissue association, cells lose their telomerase activity. As has now been shown, the individual cells recover again after the formation of tissue-like bodies, the primmorphs, and become telomerase-positive again.

3.4. Immunocytochemical Detection of BrdU Incorporation in Cells of Primmorphs

BrdU labelling and the detection approach were used in order to show that those cells which have organised themselves into primmorphs regain their ability to proliferate. As a measure of proliferation, the cells were incubated with BrdU for 12 hours. After that, the incorporation of BrdU into the DNA was determined and quantified by means of an anti-BrdU monoclonal antibody, as described above. Cells which have incorporated BrdU into their DNA are characterised by a dark (dark brown) stained cell nucleus (FIGS.

3B–D). Controls which were not incubated with the primary antibody against BrdU are not stained (FIG. 3A).

Suspensions of individual cells which were kept in CMFSW-E for one day did not contain any cells which went through DNA synthesis (Table 1). The percentage of BrdU-positive cells obtained from cell aggregates which are formed after one day from a suspension of individual cells in culture is low (6.5%). On the other hand, the number of cells synthesising DNA/proliferating in primmorplis is high. As summed up in Table 1, the proportion of BrdU-positive cells in primary primmorphs is 33.8% and in secondary primmorphs 22.3%. These figures confirm that the cells which are organised into primmorphs undergo DNA synthesis and afterwards regain their capacity for cell division.

3.5. Immunocytochemical Detection of Proliferation in Cells of Primmorphs

In order to determine whether the cells do in fact divide after the DNA synthesis, the same batches were analysed which were also used to detect the incorporation of BrdU into cells from the primmorphs of S. domuncula. Those cells which were positive for BrdU and which were still in the binuclear stage after undergoing mitosis were counted.

The results show that no binuclear stages occur in suspensions of individual cells or cell aggregates, whereas in primary primmorphs 19.4% are present in binuclear stages, and 13.8% are in binuclear stages in secondary primmorphs (Table 1).

This proves that cells in primmorphs also undergo cell division in addition to DNA synthesis.

3.6. Association of Bacteria With Cells in Primmorphs

It is known that virtually all species of sponges live in a symbiosis-like relationship with microorganisms [Müller W. E. G., Zahn R. K., Kurelec B., Lucu C., Müller I., Uhlenbruck G. (1981) J. Bacteriol. 145, 548–558]. Not only prokaryotic, but also eukaryotic organisms are found which live in association with the host (sponge, coral or other invertebrates). The organisms present in the sponges can be detected by PCR analysis [Althoff K., Schütt C., Steffen R., Batel R., Müller W. E. G. (1998) Marine Biol. 130, 529–536] and/or by analysing the rRNA in agarose gel. Whereas prokaryotic rRNA contains two main species, 23S and 16S rRNA, the two main species found in eukaryotic rRNAs are 28S and 18S rRNA.

The analysis of tissue samples after the extraction of the rRNA and subsequent separation in the agarose gel shows that, in S. domuncula, apart from the two host rRNAs, 28S and 18S rRNA, also prokaryotic rRNAs, 23S and 16S rRNA, are found (FIG. 4; lane a). After dissociation and subsequent production of primmorphs in culture, the prokaryotic rRNAs, 23S and 16S rRNA, are usually also detected (FIG. 4; track lane b).

This shows that primmorphs can also contain microorganisms without this causing any "contamination of the culture".

3.7. Detecting DNA Synthesis and Cell Proliferation in Primmorphs From Cells From the Soft Coral D. hemprichi In line with the details provided for primmorphs from the sponge S. domuncula, primmorphs from the soft coral D. hemprichi were also grown in culture.

The results show that in suspensions of individual cells or cell aggregates, no or few cells are positive for BrdU insertion, whereas both in primary primmorphs and in secondary primmorphs a large number of cells are BrdU-positive, i.e. undergo DNA synthesis (Table 1).

In addition, it was found that in single-cell suspensions or cell aggregates, no binuclear stages occur, whereas in primary primmorphs 12.9% binuclear stages and in secondary primmorphs 8.2% binuclear stages are present. Thus it has also been shown for D. hemprichi that cells in primmorphs also undergo cell division in addition to DNA synthesis (Table 1).

TABLE 1

Analysis of the cells for DNA synthesis by means of BrdU labelling and the "detection kit". The sponge S. domuncula and the soft coral D. hemprichi were used as models. The suspension of individual cells was incubated with BrdU; the nucleotides incorporated were made visible immunologically by means of anti-BrdU monoclonal antibodies. The percentage of BrdU-positive cells and of binuclear stages is shown for each batch series. The analysis was performed with: (i) dissociated cells which were kept for 1 day in CMFSW-E, (ii) cell aggregates from a suspension of individual cells after one day in culture in seawater, (iii) primary primmorphs [formation after 10 days] and (iv) secondary primmorphs [formed from one-month-old primary primmorphs after dissociation into individual cells and subsequent formation of secondary primmorphs]. 300 cells were counted per batch.

| Cells analysed: | Suberites domuncula | | Dendronephthya hemprichi | |
| --- | --- | --- | --- | --- |
| | Percentage of BrdU-positive cells | Binuclear stages | Percentage of BrdU-positive cells | Binuclear stages |
| Single cells [dissociated after 24 hours] | 0% | 0% | 0% | 0% |
| From aggregates [after 24 hours] | 6.5% | 0% | 6.5% | 0% |
| Primary primmorphs | 33.8% | 19.4% | 21.7% | 12.9% |
| Secondary primmorph | 22.3% | 13.8% | 18.5% | 8.2% |

4. Description of the Use of the Method

The use of the method of preparing the primmorph culture will be described with reference to the example of S. domuncula. The effects shown here were also found in primmorphs from D. hemprichi and are therefore valid for this species in particular and for sponges [Porifera] and corals [and for Cnidaria in general] and then also for invertebrates in general.

The primary primmorphs were obtained from individual cells from S. domuncula and used for the experiments after 21 days.

4.1. Using Primmorphs to Identify Substances Modulating DNA Synthesis and Proliferation The effect of phorbol ester on DNA synthesis and cell proliferation is well documented for vertebrates [Parker P. J., Dekker L. V. (1997) Protein Kinase C. Springer-Verlag, New York]. The (One) target enzyme of these substances is Protein Kinase C. In the course of preliminary work, we were able to show that sponges likewise possess this enzyme [Kruse M., Gamulin V., Cetkovic H., Pancer Z., Müller I. M., Müller W. E. G. (1996) J. Molec. Evol. 43, 374–383].

For this reason, the influence of a phorbol ester, phorbol 12-inyristate 13-acetate (PMA), on the percentage of BrdU-positive cells in primmorphs from S. domuncula was determined. The primmorphs were incubated for two days with different concentrations of PMA. After that, the DNA synthesis was determined by means of BrdU labelling as described above. The control, percentage of BrdU-positive cells in primmorphs without the test substance, was set at 100%. The results, which are collected in FIG. 5, show that in the concentration range from 0.01 to 1 μg PMA/ml, there is a distinct percentage increase in the number of BrdU-positive cells in primmorphs (FIG. 5).

On the basis of these data, it can be concluded that primmorphs are an excellent system for detecting biologically active substances in invertebrates, in this case those which have an effect on DNA synthesis.

In line with the above comments, it was also examined in parallel batches whether any change in proliferation occurred after incubation with the agent used here. It was possible to show that, in the range from 0.01 to 1 µg PMA/ml, there was an increase in the proliferation of cells in primmorphs.

4.2. Using Primmorphs to Analyse Environmentally Harmful Substances

Cadmium is an environmental toxin which is frequently found in the environment, and especially in an aquatic milieu [Clark R. B. (1997) Marine pollution. Clarendon Press, Oxford]. This heavy metal was selected to show that the capacity for DNA synthesis declines as a consequence of the influence of cadmium on the primmorphs.

The concentrations selected were those also encountered in the natural environment, e.g. in the Northern Adriatic. On the basis of published data, cadmium concentrations of between 0.1 ng/ml (south of Rovinj [Istria]) and 0.5 ng/ml (Pula-Siporex [Istria]) were chosen [Mikulic N. (ed.) (1994) Monitoring programme of the Eastern Adriatic Coastal Area (1983–1991). United Nations Environmental Programme, MAP Technical Reports Ser. 86, p. 2751]; in addition, higher concentrations were also used.

The results show that, after cadmium at a concentration of 1 ng/ml and more has had time to take effect, a decline in the percentage of BrdU-positive cells can be measured (FIG. 6). It should be emphasised that (i) this exposure was unique and (ii) in the environment, this heavy metal accumulates in animals; the accumulation can reach a factor of 17,500-fold [Müller W. E. G., Batel R., Lacorn M., Steinhart H., Simat T., Lauenroth S., Hassanein H., Schröder H. C. (1998) Marine Ecol. Progr. Ser., in print].

On the basis of the experimental data documented here and of those from the literature regarding the accumulation of heavy metals in aquatic organisms, it must be assumed that the system of the primmorphs is a sensitive indicator of environmental pollution.

4.3. Production of Suberitine, a Toxic Protein, in Primmorphs

The proof that suberitine is formed in S. domuncula specimens has been provided in the literature [Cariello L., Zanetti L. (1979) Comp. Biochem. Physiol. 64C: 15–19]. These sponge specimens were caught in nature. Suberitine is a toxic protein which also possesses haemolytic properties [Cariello L., Zanetti L. (1979)].

It has now been demonstrated for the first time—in the present specification—that sponge cells can also produce biologically active substances in vitro. Primmorphs from S. domuncula were cultured. The biological activity was determined in extracts from the primmorphs after 0 to 20 days [transfer of the primmorphs to the 24-well plates]. Haemolytic activity was chosen as the parameter. Raw extracts were prepared from the primmorphs in accordance with the details provided by Cariello and Zanetti (1979), and the haemolytic activity was determined by spectrophotometry. 0.1 optical unit is defined here as 1 arbitrary unit, the HU (haemolytic unit). As documented in FIG. 7, primmorphs possess a slight biological activity of 3.5±0.4 HU/mg protein on the day of the transfer to 24-well plates. After the primmorphs have been cultured for a period of more than 3 days, there is a significant increase (P<0.001) in biological activity on 6.9±0.7 HU/mg; after an incubation period of 10 days, the biological activity reaches its maximum.

On the basis of the experimental data documented here, it must be assumed that primmorphs are excellent producers of biologically active substances in vitro.

The biologically active substances are produced by the primmorphs on a small (1 ml) or large scale (20 l); in addition, production can also take place in large bioreactors and likewise in aquaculture.

TABLE 2

Increase in the size of the primmorphs and in their percentage share of BrdU-positive cells after the addition of homologous cells (from S. domuncula), and also heterologous cells (from Geodia cydonium) which were killed apoptotically by heat shock. The size of the primmorphs is indicated by the corresponding diameter. The killed cells ($1 \times 10^3$ cells per well) were added to the cultures for three days, after which the results were evaluated. 10 primmorphs in each case were measured (the averages and also the standard deviations are shown); 300 cells per batch were counted for BrdU-positive cells. The sizes before the addition of the cells and after incubation were determined (the same primmorphs were evaluated).

| | Without addition | | +S. domuncula | | +G. cydonium | |
|---|---|---|---|---|---|---|
| | Size (µm) | BrdU-positive (%) | Size (µm) | BrdU-positive (%) | Size (µm) | BrdU-positive (%) |
| Primmorphs from S. domuncula | 228 ± 39 | 31.0 | 329 ± 41 | 42.9 | 287 ± 44 | 53.8 |

4.4. Identification of Nutrients Which Make it Possible to Increase DNA Synthesis and/or Cell Proliferation in Primmorphs It has been explained above that primmorphs undergo DNA synthesis and cell proliferation in seawater/antibiotic solution without the addition of the standard nutrient media, such as serum.

It will now be shown that both the size of the primmorphs and their percentage share of BrdU-positive cells can be significantly (P<0.001) increased by the addition both of homologous cells (from S. domuncula), and also of heterologous cells (e.g. from Geodia cydonium) which have been killed apoptotically by heat shock (Table 2).

In addition, it was surprisingly discovered that phosphatidyl serine and also phosphatidylinositol cause the size of the primmorphs to increase and also lead to a rise in their percentage share of BrdU-positive cells. The following explanation was found for this. The cells killed apoptotically by heat shock (which serve as a source of nutrients) expose phosphatidyl serine and also phosphatidylinositol and other lipids on the surface of their cells. These apoptotically modified cells/membranes are phagocytised by the primmorphs.

This thus proves that both killed cells and pure components, such as lipids or even collagen or other extracellular molecules have a positive effect on the size of the cells and their percentage share of BrdU-positive cells.

4.5. Primmorphs as a Model for Finding Substances Which Modulate Telomerase Activity It is known that tumour cells possess high telomerase activity [Hastie N. D., Dempster M., Dunlop A. G., Thompson A. M., Green D. K., Allshire R. C. (1990) Nature 346, 866–868]. One objective of medical research is to reduce the activity of this enzyme in tumour cells. Because of the fact that sponge cells are telomerase-positive, the model of the primmorphs is therefore ideally suited for testing substances which reduce this activity.

In the following table, it is shown that telomerase activity in cells from primmorphs can indeed by modulated. As the agent, we used antibodies against the integrin protein cloned by us from S. domuncula and prepared recombinantly. As shown in Table 3, these antibodies reduce the telomerase activity in primmorphs after only 2 days in culture.

This thus shows that primmorphs are an excellent model for finding substances which modulate telomerase activity.

TABLE 3

Telomerase activity in cells from S. domuncula after the addition of antibodies (rabbit-polyclonal) to primmorphs. 50 µl of antibodies per well were added to the batches. The telomerase activity is stated in TPG (total product generated) and standardised to $5 \times 10^3$ cell equivalents.

| Primmorphs | Incubation time (days) | Telomerase activity Without antibodies | Telomerase activity With antibodies |
| --- | --- | --- | --- |
| + | 0 | 4.9 ± 0.6 | 4.6 ± 0.7 |
| + | 1 | 4.6 ± 0.5 | 4.3 ± 0.6 |
| + | 3 | 4.5 ± 0.5 | 3.9 ± 0.4 |
| + | 10 | 4.8 ± 0.7 | 1.2 ± 0.1 |
| + | 15 | 4.4 ± 0.4 | 0.8 ± 0.1 |

4.7. Using the Primmorphs for Culturing in Aquaculture

Primmorphs can be used for culturing larger tissue cultures and for culturing entire corresponding organisms. Use is made of aquaculture for this purpose. After an incubation period, usually of two months, in "culture chamber slides" [(Nunc)—catalogue number 177453], for example, primmorphs are transferred together with the latter to larger artificial containers (such as tanks), or directly into nature (aquatic milieu).

If larger artificial containers (such as tanks) are used, these are filled with artificial seawater, as in the case of S. domuncula, and blended with the usual trace minerals. Usually once a week, a little organic material, such as tuna fish for example, is added to the medium. After an average of one month, the primmorphs have grown into organism-like structures 5 mm in size. Longer incubation times lead to further growth to the complete organism.

This thus shows that complex organisms can form again from primmorphs kept in aquaculture. In this way, farms of sponges, corals and other invertebrates can be established, either in artificial containers (such as tanks) or in nature.

4.8. Preparing Cell Libraries

Before a cell library is established, it is necessary to check whether cells, e.g. from S. domuncula, will survive freezing and subsequent thawing and will then be capable of functioning again.

For this reason, cells were harvested and frozen, either directly after their dissociation from the starting organism, e.g. the sponge S. domuncula, or from primmorphs. To this end, the cells are frozen slowly (usually 1° C./min) in a suitable tube, usually in dimethyl sulphoxide (usually 10% in seawater) or glycerine (usually 20% in seawater). The number of cells is adjusted to about $5 \times 10^6$ cells/ml. Once a temperature of about $-70°$ C. is reached, the cells are subsequently transferred to liquid nitrogen and can be stored like this for more than six months.

When the cells are thawed again, they can be raised in stages to temperatures above $+0°$ C. Then the cells are transferred to seawater, usually being added drop by drop. When a temperature is reached which the cells also usually require in culture, aggregates and primmorphs can be established again. No major loss of vitality has been found as a result of the freezing and thawing process. Furthermore, after the formation of aggregates/primmorphs, the cells exhibit both DNA synthesis and proliferation.

This thus shows that cells from sponges, corals and other invertebrates can be deep-frozen. The possibility therefore also exists of shipping cells in a conventional manner (e.g. in dry ice). Cells can thus be cultured at a central location, i.e. cell libraries can be established.

DESCRIPTION OF THE DRAWINGS

FIG. 1. Formation of primmorphs from cells of the sponge Suberites domuncula. A. a sample of S. domuncula; magnification×1. The cells are dissociated by treatment in CMFSW-E. After two days in culture, cell aggregates form [medium: seawater/antibiotics] B which increase in size [photographed after three to four days] C; ×10 Usually after five days, primmorphs form D; ×10. E and F, cross-sections through a primmorph show the multicellular epithelium-like position of pinacocytes surrounding the inner part, which consists of spherulous cells, amoebocytes and archaeocytes; E: ×20; F: ×45.

FIG. 2. Telomerase activity in cells from S. domuncula. The telomerase activity was determined (i) in cells from tissue (lane a), (ii) in a suspension of individual cells [the cells were analysed for 14 hours,] (lane b) and (iii) in primmorphs (lane c). Defined quantities of material, corresponding to $5 \times 10^3$ cell equivalents, were incubated in the TRAP batch. After PCR amplification, the products were separated in a non-denaturing polyacrylamide gel; the gel was stained with SYBR Green I in order to make the DNA fragment visible.

FIG. 3. Cells from primmorphs with the aim of detecting DNA synthesis there. For this purpose, the primmorphs were incubated in BrdU (further details in the text); in the process, BrdU is incorporated into the DNA—if any DNA synthesis has occurred. The BrdU units incorporated are detected by means of an antibody reaction with the help of the "BrdU-labeling and detection kit". These appear as dark patches which mark the nucleus of the cell. B–D: cells from primmorphs which have been incubated with BrdU and subsequently treated with the identification reagent in order to detect BrdU. In FIG. 3D one BrdU-positive cell is shown, indicated by an arrow; one BrdU-negative cell is marked by an arrow head.

FIG. 4. Analysis of tissue samples and primmorphs for rRNA. The material was extracted and the RNA subsequently separated in the agarose gel. In addition to the two eukaryotic host rRNAs [euc], 28S and 16S rRNA, prokaryotic rRNAs [proc], 23S and 16S rRNA, are also made visible by ethidium bromide.

FIG. 5. Influence of the phorbol ester phorbol 12-myristate 13-acetate (PMA) on the percentage share of BrdU-positive cells in primmorphs from S. domuncula. The primmorphs were incubated for two days with different concentrations of PMA. After this, DNA synthesis was determined by means of BrdU labelling. The control, percentage share of BrdU-positive cells among primmorphs without the test substance, was set at 100%. 300 cells were counted per batch.

FIG. 6. Influence of cadmium, concentrations between 0.1 ng/ml and 100 ng/ml were chosen, on the amount of the percentage share of BrdU-positive cells among primmorphs.

FIG. 7. Production of suberitine, a toxic protein, in primmorphs from S. domuncula. Primmorphs were cultured. After 0 [transfer of the primmorphs to the 24-well plates] to 20 days, primmorphs were removed and tested for biological activity. For each incubation point, primmorphs were removed in rive parallel batches, a raw extract was prepared and tested for haemolytic activity. The titre, stated in HU (haemolytic units), relates to 1 mg of protein extract. The average values are shown with the standard deviations.* (P<0.001).

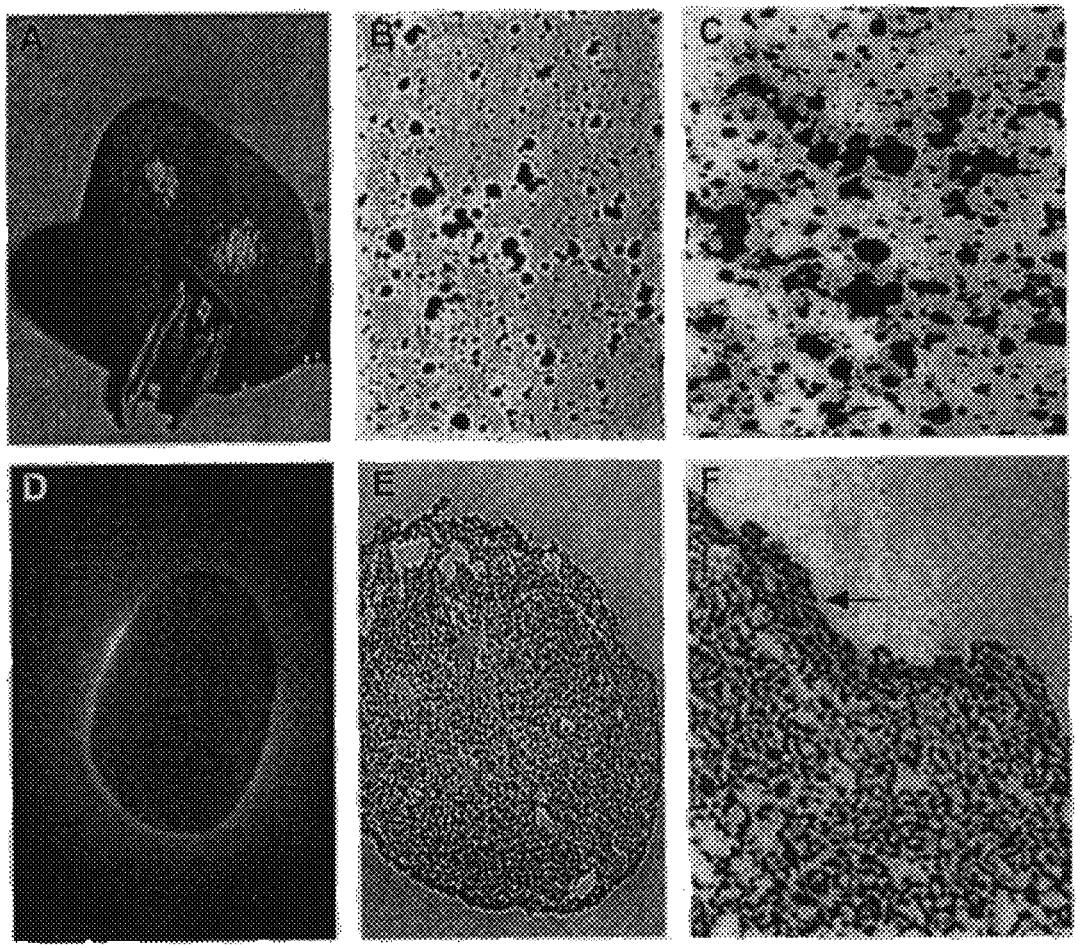

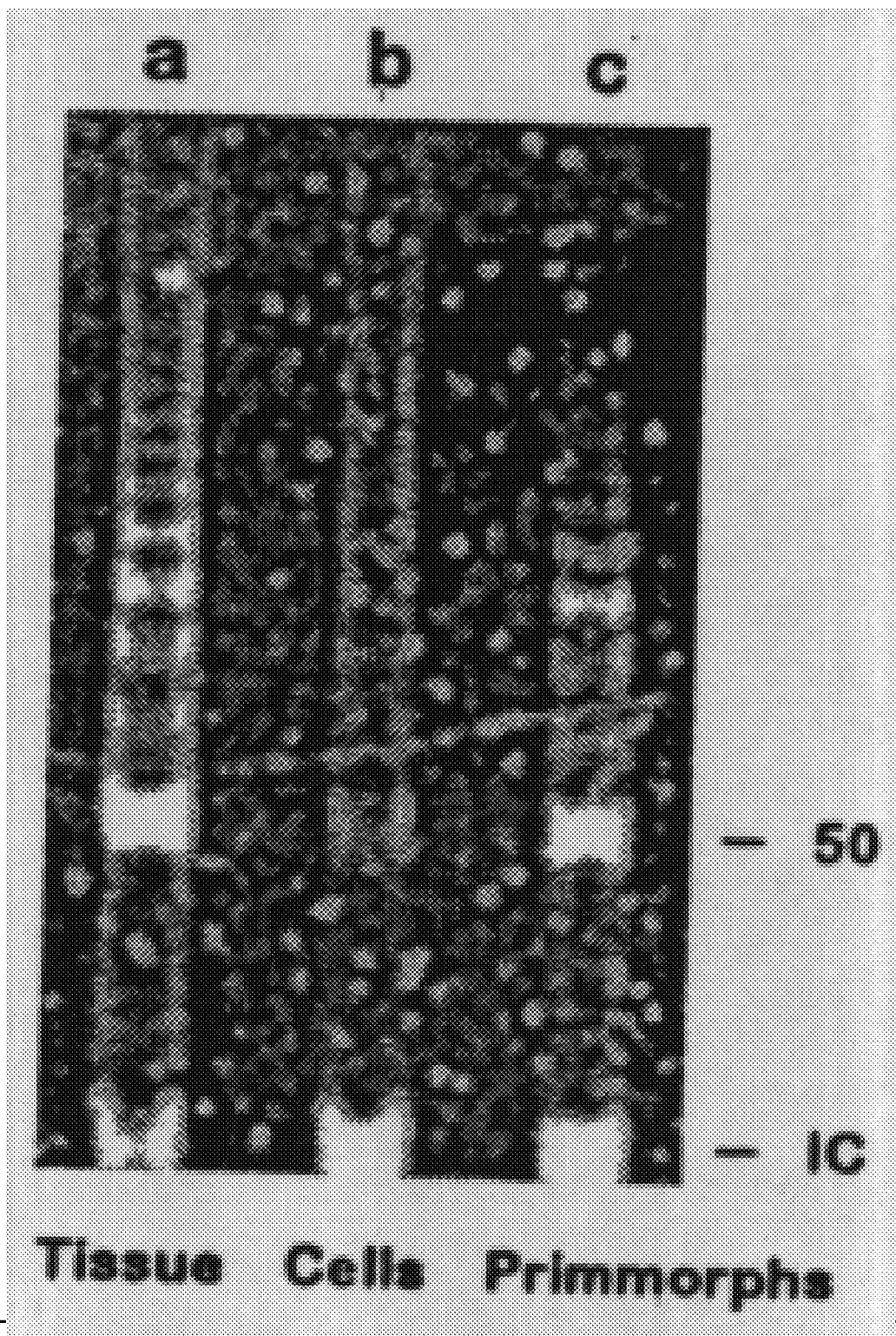

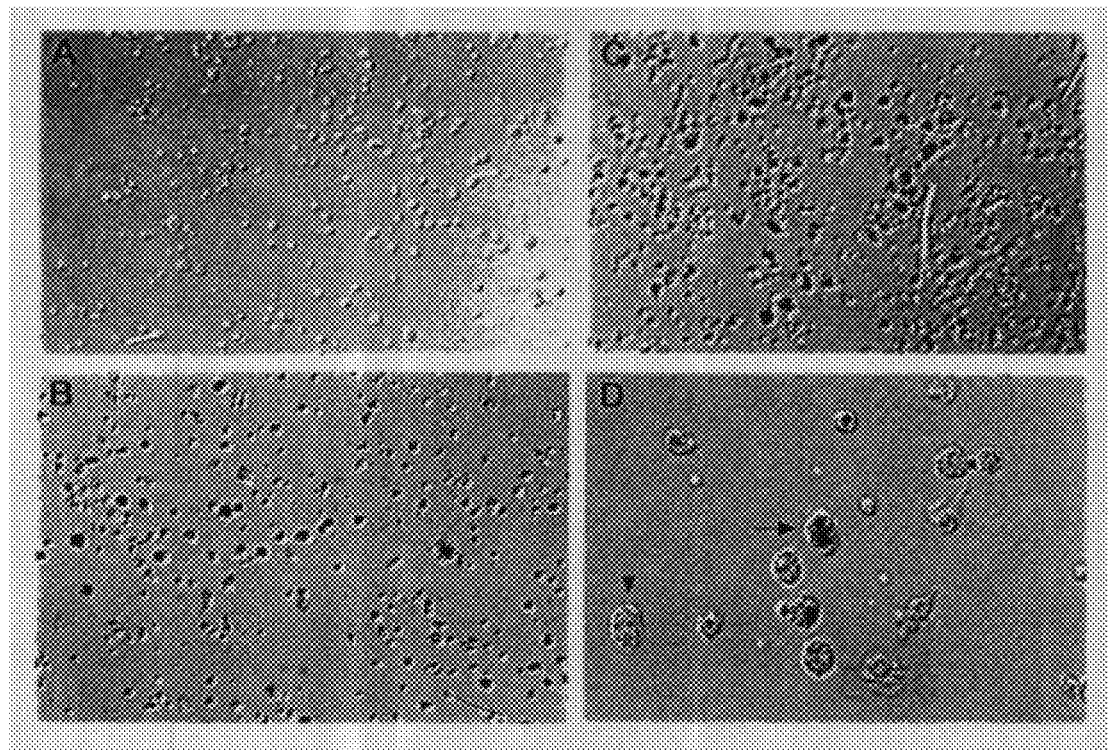

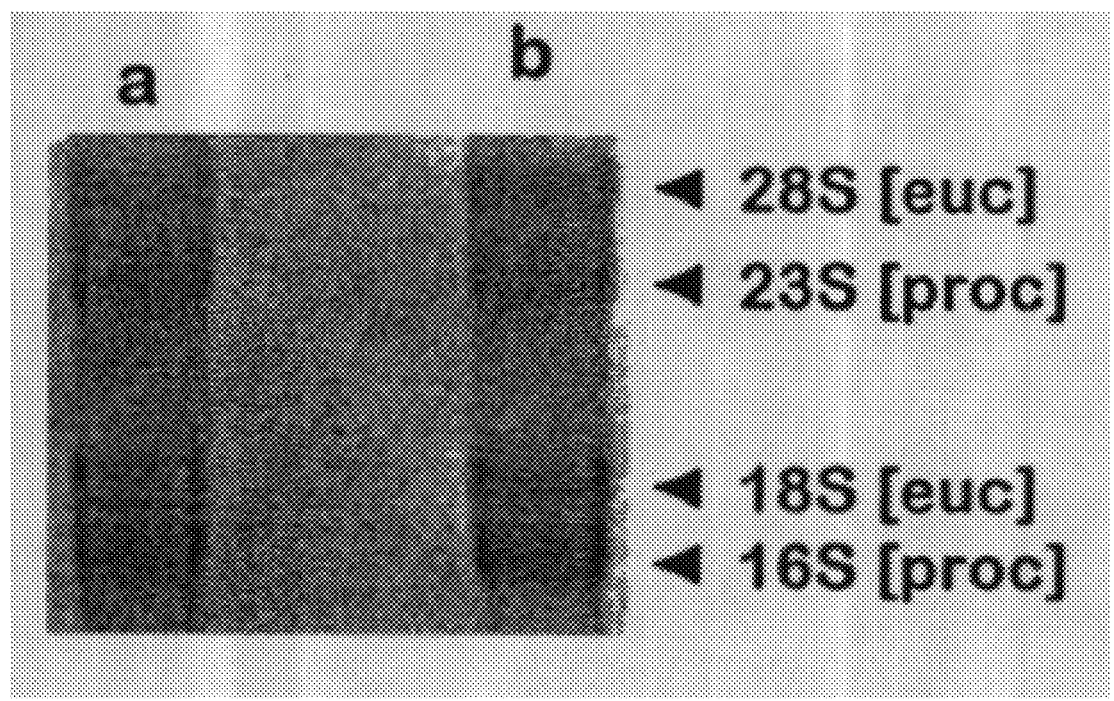

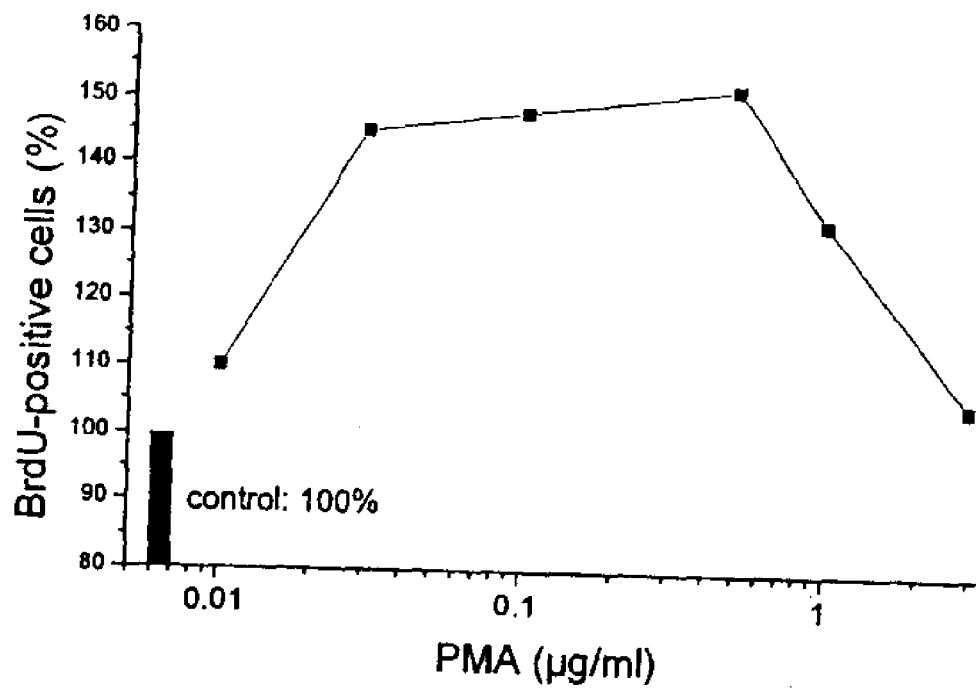

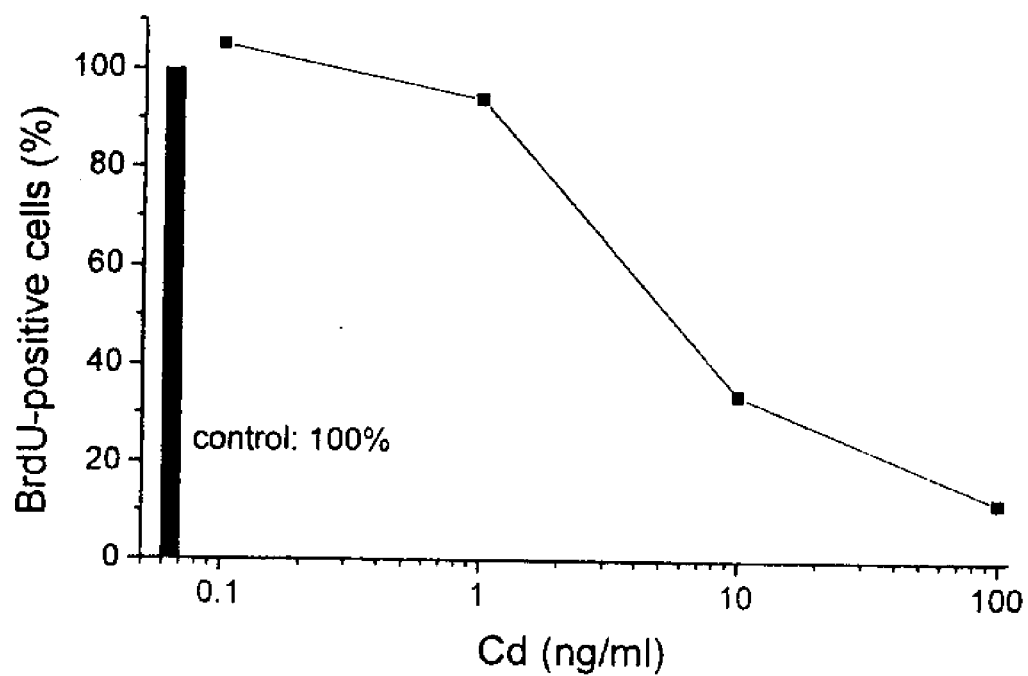

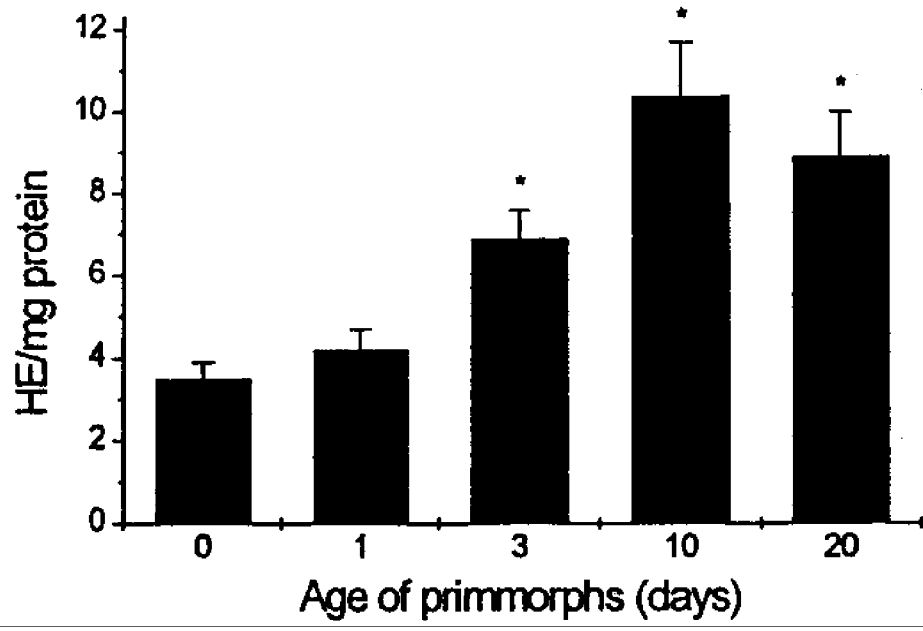

What is claimed is:

1. A method of preparing and culturing primmorphs from sponges and corals, said method comprising the steps of:

(1) cutting tissue samples of sponges or corals into pieces of tissue of approximately 0.5–1 mm$^3$, (2) transferring said pieces of tissue to a volume of $Ca^{2+}$ and $Mg^{2-}$-free seawater containing ethylene diamine tetra-acetic acid, (3) gently rotating said volume of $Ca^{2+}$ and $Mg^{2-}$-free seawater containing said pieces of tissue whereby a supernatant containing cells is produced, (4) filtering the supernatant containing the cells through a net, and trapping the cells in suspension in a culture tube, (5) repeating step (4), (6) combining the cell suspensions of step (5) to yield a combined cell suspension, (7) incubating the combined cell suspension in a seawater/antibiotic solution comprising approximately 100 IU penicillin and 100 µg/ml streptomycin, (8) adjusting the incubated cell suspension to a high cell density of approximately $10^7$ cells/ml, and (9) transferring 1 ml of said adjusted cell suspension and approximately 5 ml of said seawater/antibiotic solution to a Petri dish,

(10) incubating the Petri dish at approximately 16° C. for approximately 24 h, whereby cell aggregates that have not adhered to the dish are formed,

(11) collecting said formed cell aggregates, and washing them in seawater/antibiotic solution comprising settlement by gravity,

(12) transferring said formed cell aggregates to a new Petri dish and carefully resuspending the cells in approximately 5 ml of said seawater/antiobiotic solution,

(13) repeating steps (10) to (12) approximately 4 times,

(14) removing the primmorphs formed from said cell aggregates and culturing them in seawater or seawater/antibiotic solution with added nutrients, thereby ensuring that (a) the cells associated in the resulting primmorph retain their ability to perform DNA synthesis and/or cell proliferation and (b) an in vitro culture of proliferating cells is achieved.

* * * * *

UNITED STATES PATENT AND TRADEMARK OFFICE
CERTIFICATE OF CORRECTION

PATENT NO.   : 6,664,106 B1
DATED        : December 16, 2003
INVENTOR(S)  : Werner E.G. Mueller It is certified that error appears in the above-identified patent and that said Letters Patent is hereby corrected as shown below:

Drawings,
Please insert Figs. 1 - 7, as per attached drawing sheets 1-7.

Signed and Sealed this

Twenty-seventh Day of July, 2004

JON W. DUDAS
*Acting Director of the United States Patent and Trademark Office*